United States Patent [19]

Karaki et al.

[11] Patent Number: 4,480,636
[45] Date of Patent: Nov. 6, 1984

[54] ENDOSCOPE WITH IMAGE CORRECTION MEANS

[75] Inventors: Kouichi Karaki, Hachioji; Kenichi Oinoue, Tokyo; Takashi Tsukaya, Hachioji; Katsumi Terada, Hachioji; Masafumi Yamasaki, Hachioji; Atsushi Yusa, Hachioji; Kazuo Nakamura, Hachioji, all of Japan

[73] Assignee: Olympus Optical Co., Ltd., Japan

[21] Appl. No.: 395,629

[22] Filed: Jul. 6, 1982

[30] Foreign Application Priority Data

Jul. 9, 1981 [JP] Japan ................... 56-107483

[51] Int. Cl.³ ............................................. A61B 1/06
[52] U.S. Cl. ................................... 128/6; 358/98
[58] Field of Search ........................ 128/4–8; 358/98, 163, 213

[56] References Cited

U.S. PATENT DOCUMENTS

| 4,237,488 | 12/1980 | Takemura | 358/163 |
| 4,253,120 | 2/1981 | Levine | 358/163 |
| 4,253,447 | 3/1981 | Moore et al. | 128/6 |
| 4,300,163 | 11/1981 | Wada et al. | 358/163 |
| 4,340,909 | 7/1982 | Yamada et al. | 358/213 |
| 4,344,091 | 8/1982 | Gardner et al. | 358/213 |

Primary Examiner—Edward M. Coven
Assistant Examiner—Max F. Hindenburg
Attorney, Agent, or Firm—Parkhurst & Oliff

[57] ABSTRACT

In an endoscope for displaying an image of an object on a monitor screen, a static induction transistor (SIT) image sensor having a number of light receiving elements is arranged at a light emitting side of an image guide bundle. In order to eliminate dead spots appearing in the displayed image due to broken fibers in the image guide bundle, pixel signals of light receiving elements corresponding to the dead spots are formed by interpolation with the aid of pixel signals derived from light receiving elements adjacent to the relevant light receiving elements to be interpolated. As an interpolation function, for example, an average of the pixel signals derived from the adjacent light receiving elements is used. The addresses of the light receiving elements corresponding to the dead spots are stored previously in a PROM during a manufacturing stage. In this manner, the interpolated image of the object having an excellent image quality can be displayed on the monitor.

21 Claims, 8 Drawing Figures

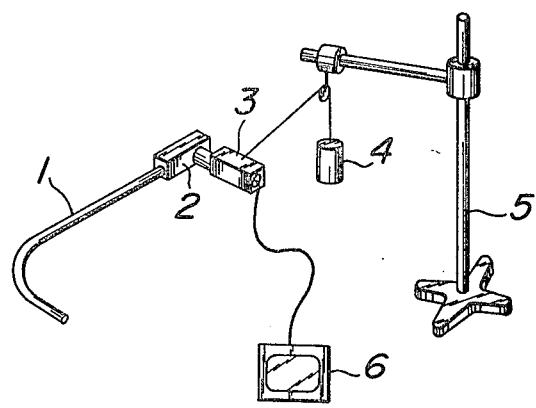
FIG_1
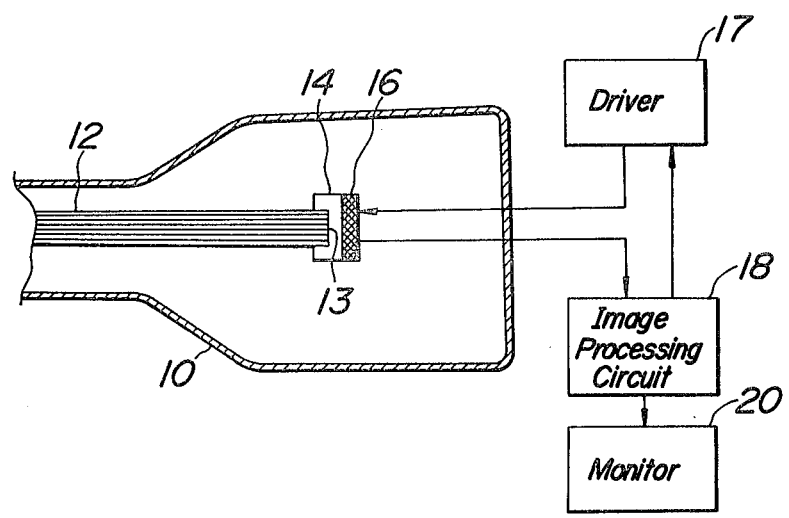
FIG_2

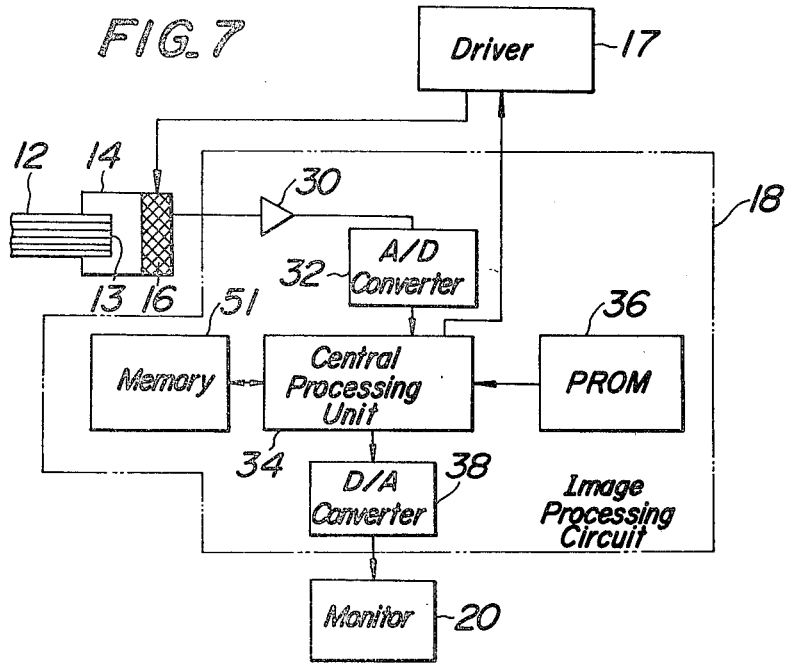
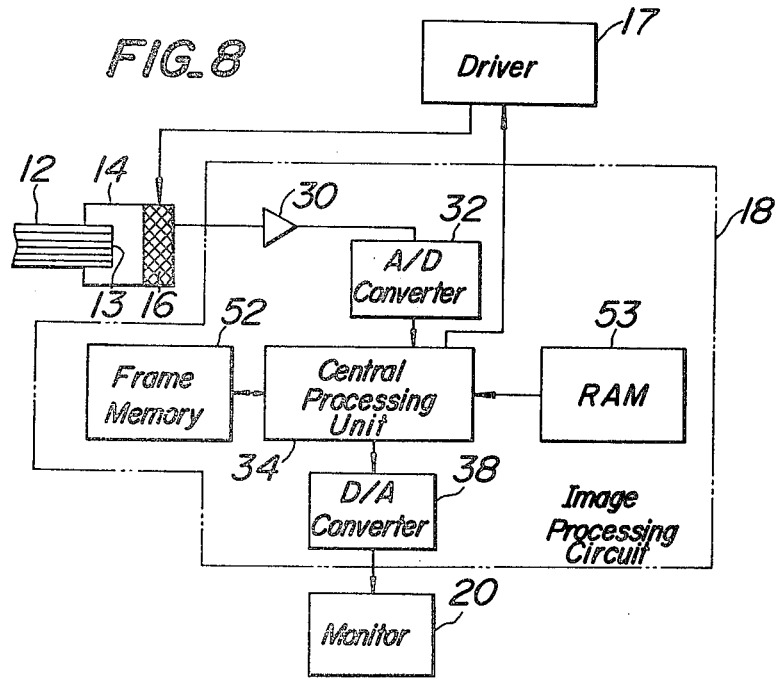

ENDOSCOPE WITH IMAGE CORRECTION MEANS

BACKGROUND OF THE INVENTION

The present invention relates to an endoscope for inspecting interior constructions and structures of various organs of human beings, industrial products, etc., and more particularly to an endoscope comprising an image guide bundle, a solid state image sensing device and a monitor for displaying interior structure images having a high image quality.

FIG. 1 shows a typical known endoscope with a monitor comprising a protection tube 1 in which an image guide bundle having a plurality of optical fibers is inserted, a main body 2 to which a television camera 3 supported by a balancer 4 and a stay 5 is secured, and a monitor 6. For instance, the tube 1 is inserted into a stomach through an esophagus and an image of an inner wall of the stomach may be displayed on the monitor 6. In such an endoscope since there are usually broken optical fibers in the image guide bundle, dead spots, i.e. black dots appear in the image displayed on the monitor 6 and thus, the image quality is decreased to a great extent. Usually the image guide bundle includes about forty thousands optical fibers each having a diameter of about 5 $\mu$m and arranged regularly. Therefore, in practice, it is not possible to eliminate an occurrence of broken fibers during a manufacturing stage thereof. If the image transferred through the image guide bundle including such broken fibers which can not transfer or transmit light rays is picked up by the TV camera 3 and is displayed on the monitor 6, black dead spots appear in the displayed image and a quality of the image is deteriorated. It should be further noted that broken fibers are produced not only during the manufacturing process, but also during actual usages of the endoscope.

Moreover since the TV camera 3 arranged in front of a light emitting side of the image guide bundle has a higher resolution as compared with a fiber pitch thereof, portions which can not transfer light rays are formed on boundaries between respective fibers each having usually a hexagonal shape due to clads, so that a so called mesh defect is generated in the display image. In this manner, the quality of the image displayed on the monitor 6 is further made lower.

SUMMARY OF THE INVENTION

The present invention has for its object to remove the drawbacks mentioned above and to provide an endoscope which can display an image having no dead spot, even if an image guide bundle includes broken fibers.

It is another object of the invention to provide an endoscope which can display an image having no mesh defect, even if a resolution of an image sensor is higher than an image guide bundle.

It is still another object of the invention to provide an endoscope which can display an image of good quality by means of a simple construction.

According to the invention, an endoscope for displaying an image of an object to be inspected comprises means including an image guide bundle having a number of optical fibers for transmitting the image of the object from a distal end to a light emitting end of the image guide bundle;

means including a solid state image sensing device having a number of light receiving elements arranged to receive the image of the object transmitted through the image guide bundle to produce pixel signals;

memory means for storing at least one address of a light receiving element which corresponds to a part of the image guide bundle which part does not transmit a light flux effectively;

means for correcting a pixel signal of the light receiving element whose address is stored in said memory means to product a corrected pixel signal and for reconstructing a corrected image signal from the corrected and non-corrected pixel signals; and monitor means for receiving the corrected image signal to display a corrected image of the object.

BRIEF DESCRIPTION OF THE DRAWINGS

FIG. 1 is a perspective view showing a known endoscope with a monitor;

FIG. 2 is a schematic view illustrating one embodiment of a light emitting side of an image guide bundle in the endoscope with a monitor according to the invention;

FIG. 7 is a block diagram showing another embodiment of the image processing circuit according to the invention; and FIG. 8 is a block diagram illustrating still another embodiment of the image processing circuit according to the invention.

DESCRIPTION OF THE PREFERRED EMBODIMENTS

Figure 3:
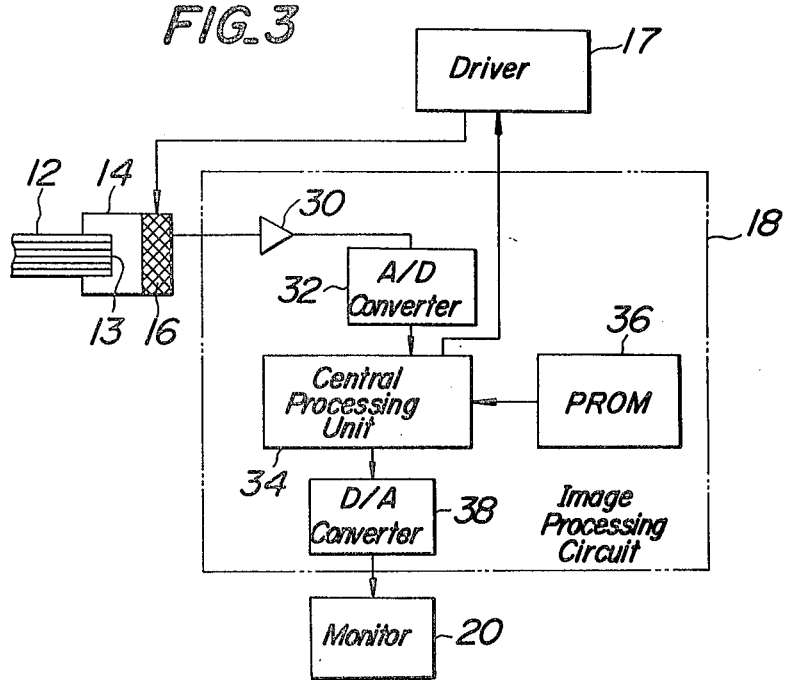
FIG. 3 is a schematic view depicting one embodiment of an image processing circuit according to the invention.

In a preferred embodiment according to the invention, use is made of a SIT (Static Induction Transistor) image sensor as a solid state image sensing device. The SIT image sensor comprises photo diodes and SITs in combination as shown in, for example, IEEE Trans. Electron Devices, ED-26, 1979, "Static Induction Transistor Image Sensors", and has various superior characteristics such as highly integrated construction, good linearity over a wide output range, high sensitivity due to amplification property, and possibilities of non-destructive read-out and random access.

FIG. 2 is a schematic view showing one embodiment of the endoscope according to the invention. In FIG. 2, only a light emitting side of an image guide bundle inserted in a protection tube is shown. In FIG. 2, an image guide bundle 12 is inserted in a protection tube 10 and an image of an object to be inspected is transferred through the image guide bundle 12 from its distal end to its light emitting end 13. In this embodiment, an SIT image sensor 16 is arranged opposite to the light emitting end 13 by means of a fixing member 14 which serves to correctly position the image sensor 16 with respect to the light emitting side 13 of the image guide bundle 12. In this case, one image element (hereinafter, called simply pixel) of the image sensor 16 may be arranged corresponding to each fiber one by one. It should be noted that it is also possible to arrange a plurality of pixels corresponding to each fiber as will be explained later. Under the control of a driver circuit 17, the SIT image sensor 16 and a shutter (not shown) are driven in such a manner that the shutter is released for a given exposure time and then luminous information, i.e. pixel signals stored in the image sensor 16 is read out. The pixel signals derived from the SIT image sensor 16 are successively supplied to an image processing circuit 18. In these pixel signals, there are dead spots whose amplitude is substantially zero. According to the invention, these dead spots are compensated for by effecting an interpolation to reconstruct a corrected image signal which is then supplied to a monitor 20. In this manner, on the monitor 20 there can be displayed an image without dead spots.

According to the invention, there may be conceived the following four techniques dependent upon the manner of reconstructing the image signal.

(1) In the first technique, the pixels of the image sensor are read out successively at a relatively low rate, and immediately before a pixel corresponding to a dead spot is to be read out, pixels around the relevant pixel are read out at high speed to derive pixel signals and an interpolated pixel signal of the relevant pixel is calculated from the read out pixel signals. Then the interpolated pixel signal is supplied together with the pixel signals read out of the image sensor to the monitor at a suitable timing which is in synchronism with the read out timing of the image sensor. In this first measure, it is necessary that the image sensor has the random access and nondestructive read out functions.

(2) In the second technique, prior to read-out of the image sensor, the interpolated pixel signals are calculated from given pixel signals derived from the image sensor and are stored in a memory. In case of reading out the image sensor, the calculated pixel signals store in the memory are also read out at suitable timing to reconstruct the corrected image signal. In this second technique, the image sensor must also have the random access and nondestructive read out functions.

(3) In the third technique, interpolated pixel signals are first calculated from given read out pixel signals and then are stored in a memory together with the given pixel signals which are used to calculate the interpolated pixel signals. In this technique, the image sensor is sufficient to have the random access function, because the pixel signals from which the interpolated pixel signals are calculated are also stored in the memory.

(4) In the last technique, all the pixel signals read out of the image sensor are stored in a frame memory, and interpolated pixel signals are calculated from given pixel signals read out of the frame memory and then are stored in the frame memory at corresponding positions. After that, the frame memory is read out to derive a corrected image signal. In this last measure, since the frame memory has the nondestructive read out and random access properties, the image sensor does not need to have these properties and thus may be constituted by any kinds of the solid state image sensing device.

FIG. 3 is a schematic view showing one embodiment of the image processing circuit 18 according to the invention belonging to the first technique. The pixel signal read out of the SIT image sensor 16 is amplified by an amplifier 30, then converted into a digital signal by an A/D converter 32, and supplied to a CPU (Central Processing Unit) 34. The CPU 34 actuates the driver circuit 17 and effects a calculation for deriving interpolated pixel signals. A PROM 36 is connected to the CPU 34, and various controlling program and addresses of the pixels corresponding to the dead spots have been stored in the PROM 36. This may be effected at a final step of the manufacturing process of the endoscope. The pixel signals successively supplied from the CPU 34 are converted into analogue signals by a D/A converter 38 again and the analog signals thus converted are supplied to the monitor 20.

Figure 4:
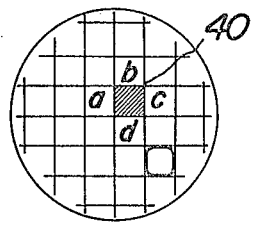
FIG. 4 is a schematic view showing a pixel arrangement including a dead spot.
Figure 5:
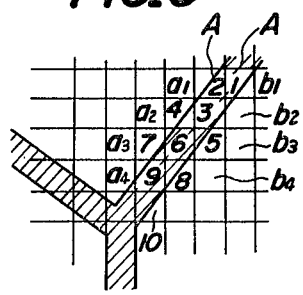
FIG. 5 is a schematic view illustrating a pixel arrangement including a mesh defect.

An operation of the image processing circuit 18 of the present embodiment will be explained with reference to FIGS. 3 to 5. For the sake of simplicity, it is assumed that each pixel of the SIT image sensor 16 is arranged corresponding to each fiber of the image guide bundle one by one as shown in FIG. 4. After the SIT image sensor 16 is secured to the light emitting end 13 of the image guide bundle through the fixing member 14 during the manufacturing stage, a light flux having a uniform light intensity is introduced from the distal end of the bundle 12, and a position of a dead spot 40, i.e. an address of the pixel at which the image can not be transferred and further if possible addresses of adjacent pixels used in an interpolation process to be explained later are stored in the PROM 36.

In case of using the endoscope actually, the pixels of the SIT image sensor 16 are successively read out by means of the driver circuit 17 under the control of the CPU 34, while the addresses of the pixels are compared with the addresses of the dead spot previously stored in the PROM 36. When such addresses correspond, pixel signals derived from the pixels a, b, c, d in FIG. 4 adjacent to the pixel corresponding to the dead spot 40 are averaged, and then a pixel signal of the pixel which corresponds to the dead spot 40 and whose address has been stored in the PROM 36 is interpolated by the average value thus obtained. Since the SIT image sensor can effect the random access and nondestructive read out, the above correction can be effected without providing a memory and thus, the circuitry can be made simple and inexpensive. Moreover, it is a matter of course that the average calculation program is stored in the PROM 36, previously.

As for an interpolation function, not only $\frac{1}{4}(a+b+c+d)$ but also $\frac{1}{2}(a+c)$, $\frac{1}{2}(b+d)$, or in the simplest case, an image of one of the pixel signal a, b, c, and d may be used as the interpolated pixel signal. Furthermore, it is also possible to use adjacent six and eight pixels in order to calculate the interpolated value. In this manner, according to the invention, any desired interpolation function can be selected at will and any desired corresponding calculation program can be stored in the PROM 36. Moreover, since, in case of using the SIT image sensor as the solid state image sensing device, the nondestructive read-out is possible and it is not necessary to store the pixel values a, b, c, and d in a RAM arranged inside or outside the CPU 34. In this manner, the pixel signal corresponding to the dead spot pixel is interpolated by the average value mentioned above, and thus the image signal having no dead spot seemingly is reconstructed and is supplied to the monitor 20 through the D/A converter 38 and, if necessary, a buffer memory, etc. Moreover, it is a matter of course that if use is made of a monitor which can generate an image from the digital signal, it is possible to supply the output signal from the CPU 34 to the monitor 20 directly.

FIG. 4 is a schematic view showing a pixel arrangement including a dead point. In FIG. 4, each each of the pixels of the SIT image sensor 16 corresponds to respective fibers of the image guide bundle 12 one by one. According to the invention it is also possible to correspond a plurality of pixels of the SIT image sensor to each of the fibers by making a pitch of the pixels of the SIT image sensor smaller than that of the image guide bundle. By means of such an arrangement, the image sensor may be easily positioned with respect to the image guide bundle. However, in this case, pixels corresponding to a boundary between respective fibers of hexagonal shape i.e. clads become dead spots as shown in FIG. 5, and the so called mesh defect is generaged in the displayed image.

According to the invention, the mesh defect can be also eliminated. In this case, addresses of pixels corresponding to the mesh defect and of a few pixels neighboring those corresponding to the mesh defect are previously stored in the PROM 36. For example, as shown in FIG. 5, addresses of pixels 1, 2, 3, 4 . . . which are at least partially situating in the mesh defect portion A and those of the neighboring pixels $a_1, a_2, b_1, b_2$ . . . are stored in the PROM 36. Under the control of the CPU 34, the pixel signals of the pixels 1 and 2 in the mesh defect portion A are interpolated by an average value $\frac{1}{2}(a_1+b_1)$, and also the pixel signals of the pixels 3 and 4 are interpolated by a value $\frac{1}{2}(a_2+b_2)$. In the same manner, the corrected image signal is reconstructed and is supplied to the monitor 20 which displays the image having no mesh defect.

In case of reconstructing the image signal having no mesh defect, the image signal may be corrected by suitably adjusting the gain or amplitude of predetermined pixel signals. For instance, a half of the pixel 2 is entered in the mesh defect and thus, the amount of the pixel signal derived from the relevant pixel 2 may be increased by twice to obtain a corrected or adjusted pixel signal. By means of such a correcting method, the original information can be utilized to the optimum extent.

Figure 6:
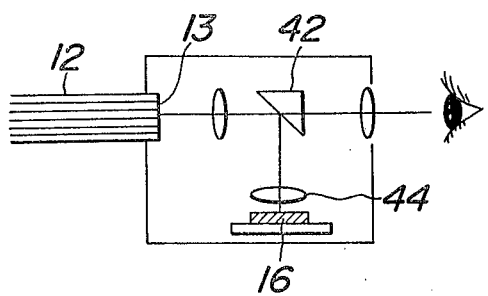
FIG. 6 is a schematic view depicting another embodiment of the endoscope according to the invention which can perform a monitoring and an observation with the naked eye simultaneously.

FIG. 6 is a schematic view showing another embodiment of the endoscope according to the invention which can perform the monitoring and observation with the naked eye simultaneously. In this embodiment, a light flux emitted from the light emitting end 13 of the image guide bundle 12 is divided into two light fluxes by a half mirror 42. Then, one light flux transmitted through the half mirror 42 is observed by the naked eye by means of an eye piece 45 and the other light flux reflected by the half mirror 42 is focussed on the SIT image sensor 16 through an objective lens 44.

Since the SIT image sensor has a high sensitivity as compared with the other image sensing devices, an intensity of light impinging on the SIT image sensor may be made smaller. Therefore, it is possible to make a light transmitting percentage of the half mirror 42 larger, and then the bright image can be observed with the naked eye.

FIG. 7 is a circuit diagram showing another embodiment of the image processing circuit 18 according to the invention. In the present embodiment the circuit 18 comprises a memory 51 for storing the corrected pixel signals. In this embodiment, after the shutter has been closed, the central processing unit 34 reads out the addresses stored in the PROM 36 and sends an address signal to the driver 17 to read out pixel signals from addressed light receiving elements of the SIT image sensor 16. It should be noted that the addressed light receiving elements are adjacent to the light receiving elements whose addresses have been stored in the PROM 36. Then, the central processing unit 34 calculates interpolated pixel signals from the read out pixel signals and the interpolated pixel signals are stored in the memory 51 together with their addresses. Next, the central processing unit 34 activates the driver 17 to read out the pixel signals from the SIT image sensor 16 which are then supplied to the monitor 20. When the light receiving elements whose addresses have been stored in the PROM 36 are to be read out, the central processing unit 34 reads out the interpolated pixel signals stored in the memory 51, instead of the pixel signals derived from the relevant light receiving elements. In this manner, the monitor 20 can receive the corrected image signal and can display the image of the object having no dead spot.

In this embodiment, the image sensing device 16 must have the nondestructive read out property as well as the random access property.

In a modified embodiment of that shown in FIG. 7, the memory 51 stores not only the interpolated pixel signals, but also the pixel signals which have been used to calculate the interpolated pixel signals. Then, it is not necessary for the image sensor to have the nondestructive read out property.

FIG. 8 is a block diagram illustrating still another embodiment of the image processing circuit 18. In this embodiment, the circuit 18 comprises a frame memory 52. At first, the central processing unit 34 activates the driver 17 to read out all the pixel signals from the image sensor 16 and the read out pixel signals are once stored in the frame memory 52. Then, the central processing unit 34 reads out the addresses stored in a RAM 53 and given pixel signals are read out of the frame memory 52 with the aid of the read out addresses. Then, the central processing unit 34 calculates interpolated pixel signals from the read out pixel signals and the calculated pixel signals are stored in the frame memory 52 at its corresponding memory positions. After that, the frame memory 52 is read out to derive the corrected image signal which is then supplied to the monitor 20 via the D/A converter 38.

In this embodiment, since the frame memory 52 can stores all the pixel signals derived from the image sensor 16, the image sensor 16 may be not of the nondestructive read out and random access type, but may be constituted by any other solid state image sensing device such as CCD and BBD. However, the SIT image sensor is preferably used, because it has superior properties such as high sensiivity, linearity, random access and nondestructive read-out. Further, since use is made of the RAM 53, even if one or more optical fibers of the image guide bundle 12 are broken during the use of the endoscope, addresses of light receiving elements corresponding to the broken fibers can be written into the RAM 53.

As mentioned above, according to the invention, since the image interpolating process is performed electrically by arranging the solid state image sensing device at the light emitting side of the image guide bundle in the endoscope, the construction is made extremely small as compared with the known pickup tube using the TV camera, and if use is made of the SIT image sensor as the solid state image sensing device it is possible to make the construction much smaller, the sensitivity higher, and the linearity of performance characteristic better.

Furthermore, since the pixel signals corresponding to the dead spots caused by the broken fibers in the image guide bundle or the mesh defect based on the boundary between respective fibers can be corrected with the aid the pixel signals derived from adjacent pixels, the dead spots or the mesh defect can be effectively removed from the image displayed on the monitor, and the image quality can be improved to a great extent.

What is claimed is:

1. An endoscope apparatus for displaying an image of an object to be inspected comprising:

means including an image guide bundle having a plurality of optical fibers for transmitting the image of an object from a distal end to a light emitting end of the bundle;

means including a solid state, random access, nondestructive read-out image sensing device having a plurality of light receiving elements arranged to receive an image of an object transmitted through said bundle to produce a plurality of pixel signals;

memory means for storing at least one address of a light receiving element which corresponds to a part of said image guide bundle which does not transmit light effectively;

means for correcting a pixel signal of said light receiving element having its address stored in said memory means for producing a corrected pixel signal and for reconstructing a corrected image signal from said corrected and other pixel signals, said means for correcting including means for successively reading addresses of the pixel signals from the image sensing device, means for comparing each of said pixel signal addresses with the stored address in said memory means to produce a coincidence signal when such addresses correspond, means responsive to said coincidence signal for reading at least one pixel signal from a light receiving element adjacent to the light receiving element having its address stored in said memory means, and means for calculating said corrected pixel signal from said at least one pixel signal; and monitor means for receiving the corrected image signal to display a corrected image of an object.

2. An endoscope apparatus according to claim 1, wherein each light receiving element of said solid state image sensing device is arranged correspondingly to each fiber of said image guide bundle one by one.

3. An endoscope according to claim 2, wherein said pixel signal correcting means is so constructed that a pixel signal of a light receiving element corresponding to an inoperative fiber which does not transmit a light flux is produced by a corrected pixel signal which is interpolated by at least one pixel signal derived from at least one light receiving element corresponding to at least one operative fiber neighboring said inoperative fiber.

4. An endoscope according to claim 3, wherein said corrected pixel signal is interpolated by a pixel signal derived from a light receiving element which corresponds to an operative fiber adjacent to said inoperative fiber.

5. An endoscope according to claim 3, wherein said corrected pixel signal is interpolated by an average of two pixel signals derived from two light receiving elemenets corresponding to two operative fibers adjacent to said inoperative fiber on both sides thereof.

6. An endoscope according to claim 3, wherein said corrected pixel signal is interpolated by four pixel signals derived from four light receiving elements corresponding to four operative fibers which surround said inoperative fiber.

7. An endoscope according to claim 3, wherein said corrected pixel signal is interpolated by six pixel signals derived from six light receiving elements corresponding to six operative fibers which surround said inoperative fiber.

8. An endoscope apparatus according to claim 3, wherein said corrected pixel signal is interpolated by eight pixel signals derived from eight light receiving elements corresponding to eight operative fibers which surround said inoperative fiber.

9. An endoscope according to claim 1, wherein a plurality of light receiving elements of said solid state image sensing device are arranged correspondingly to each fiber of said image guide bundle.

10. An endoscope according to claim 9, wherein said pixel signal correcting means is so constructed that each of pixel signals of a plurality of light receiving elements corresponding to an inoperative fiber which does not transmit a light flux is formed by a corrected pixel signal which is interpolated by at least one pixel signal derived from at least one light receiving element corresponding to at least one operative fiber neighboring said inoperative fiber.

11. An endoscope according to claim 10, wherein said corrected pixel signal is formed by an average of a plurality of pixel signals derived from a plurality of light receiving elements corresponding to at least one operative fiber neighboring said inoperative fiber.

12. An endoscope according to claim 1, wherein said pixel signal correcting means is so constructed that a gain of a pixel signal derived from a light receiving element corresponding to said part of the image guide bundle is increased to form the corrected pixel signal.

13. An endoscope apparatus according to claim 1, wherein said solid state image sensing device is constituted by a static induction transistor image sensing device.

14. An endoscope according to claim 13, wherein said pixel signal correcting means comprises means for reading out the address stored in said memory means, means for reading out at least one pixel signal from at least one light receiving element adjacent to the light receiving element whose address is stored in said memory means, means for calculating the corrected pixel signal from the at least one read out pixel signal, means for storing the corrected pixel signal and means for reading out the pixel signals from the image sensing device as well as said corrected pixel signal from said storing means to reconstruct the corrected image signal.

15. An endoscope according to claim 13, wherein said pixel signal correcting means comprises means for reading out the address stored in said memory means, means for reading out at least one pixel signal from at least one light receiving element adjacent to the light receiving element whose address is stored in said memory means, means for calculating the corrected pixel signal from the at least one read out pixel signal, means for storing the corrected pixel signal together with said at least one read out pixel signal, and means for reading out the pixel signals from the image sensing device as well as said corrected and non-corrected pixel signals from said storing means to reconstruct the corrected image signal.

16. An endoscope according to any one of claims 13 or 1, wherein said pixel signal correcting means comprises a frame memory for storing the pixel signals read out of the image sensing device, means for reading out of the frame memory at least one pixel signal which is read out of at least one light receiving element adjacent to the light receiving element whose address is stored in said memory means, means for calculating the corrected pixel signal from the at least one read out pixel signal, means for storing the corrected pixel signal at a position of the frame memory corresponding to the light receiving element whose address is stored and means for reading out the corrected image signal stored in the frame memory.

17. An endoscope apparatus according to claim 1, wherein memory means comprises a PROM in which said at least one address has been stored during a manufacturing stage of the endoscope.

18. An endoscope according to claim 1, wherein said memory means comprises a RAM in which said at least one address is stored.

19. An endoscope according to claim 1, further comprising means for effecting an observation of the image of the object with the naked eye.

20. An endoscope according to claim 9, wherein said memory means stores addresses of a plurality of light receiving elements which at least partially correspond to clads situating at boundaries between adjacent fiber cores.

21. An endoscope according to any one of claims 3, 4, 5, 6, 7, 8, 10 or 11, wherein said memory means further stores at least one address of at least one light receiving element whose pixel signal is used to form the corrected pixel signal.

* * * * *